United States Patent
Bohult

(10) Patent No.: US 7,219,253 B2
(45) Date of Patent: May 15, 2007

(54) PROCESS FOR PROVIDING SUBMODEL PERFORMANCE IN A COMPUTER PROCESSING UNIT

(75) Inventor: Stefan R. Bohult, Phoenix, AZ (US)

(73) Assignee: Bull HN Information Systems Inc., Billerica, MA (US)

( * ) Notice: Subject to any disclaimer, the term of this patent is extended or adjusted under 35 U.S.C. 154(b) by 447 days.

(21) Appl. No.: 10/837,079

(22) Filed: Apr. 30, 2004

(65) Prior Publication Data

US 2005/0246566 A1    Nov. 3, 2005

(51) Int. Cl.
*G06F 1/04* (2006.01)
*G06F 19/00* (2006.01)
*G06F 11/30* (2006.01)

(52) U.S. Cl. .............. 713/502; 713/400; 713/500; 713/502; 713/600; 702/182; 700/32; 700/108; 700/174

(58) Field of Classification Search ........... 713/400, 713/401, 500, 502, 600; 702/182; 714/47; 700/32, 108, 174; 712/206, 216, 220
See application file for complete search history.

(56) References Cited

U.S. PATENT DOCUMENTS

| | | | | |
|---|---|---|---|---|
| 4,445,776 A | * | 5/1984 | Hyatt | 355/78 |
| 6,711,672 B1 | * | 3/2004 | Agesen | 712/227 |
| 6,799,215 B1 | * | 9/2004 | Giroir et al. | 709/227 |
| 2004/0045036 A1 | * | 3/2004 | Terasaki | 725/116 |
| 2004/0225869 A1 | * | 11/2004 | Pagni et al. | 712/227 |

* cited by examiner

Primary Examiner—Rehana Perveen
Assistant Examiner—Nitin C. Patel
(74) Attorney, Agent, or Firm—Stefan R. Bohult; James H. Phillips; Russell W. Guenthner

(57) ABSTRACT

A simple and accurate processor derating method includes: sampling a real-time counter/clock too obtain an initial time value T1; resetting an Icnt Counter; incrementing the Icnt Counter to reflect the processing of each instruction; comparing the count in the Icnt Counter to a predetermined count IcntMax and if the count in the Icnt Counter is at least IcntMax, then sampling the RTC to obtain a second time T2. T1 is then subtracted from T2 to obtain a time difference DT which is multiplied by ((1−1/DF)−1) to obtain a Degradation Delay DD period, DF being a constant having a value which is the desired submodel performance with respect to full performance. The Degradation Delay is instituted, the RTC is sampled from time to time to obtain a test third time T3. When a test T3 minus T2 is not less than DD, then T1 is set to T3. Then, the procedure is repeated for a next group of instructions. Optionally, further accuracy can be achieved by treating "wait-type" and/or "RTC-access-type" instructions specially and also by calculating a DDExtra period value which is used to adjust the next DD.

2 Claims, 4 Drawing Sheets

PROCESS FOR PROVIDING SUBMODEL PERFORMANCE IN A COMPUTER PROCESSING UNIT

FIELD OF THE INVENTION

This invention relates to the art of computer systems and, more particularly, to a process for accurately achieving any selected level of submodel performance in a processing unit.

BACKGROUND OF THE INVENTION

In the delivery of computer processing power to customers or end users, it is sometimes desirable to offer a processing unit with a controlled level of performance that is less than the highest level of performance that could be achieved. For example, in the mainframe computing industry, the price charged for a processing unit is often directly related to performance, and so reducing the maximum allowable performance of a delivered unit allows the manufacturer to deliver a product at a controlled level of performance and to charge the customer a lower price than would be offered for a unit that would deliver maximum performance. This practice is common and fully accepted in the computer industry.

In a complex computer system, achieving accurate degradation of performance in a precisely controlled manner to obtain a certifiable submodel rating is a not trivial task. The problem is made complex by many factors.

Some examples of these factors are:
1) Instructions in a processor, whether implemented in hardware or in a software emulation, may not require the same amount of time for execution.
2) In a software emulation, or in the firmware to control a hardware based central processing unit, instructions used to control and perform the emulation of a processor may themselves not execute in the same amount of time each time they are executed.
3) The same series of instructions, when executed multiple times, may vary, sometimes widely, in the amount of time required to complete either single instructions or a series of instructions. This can be caused either by direct factors such as cache miss or by indirect causes such as bus interference from other programs running on another processor.
4) In offering a submodel, it is desirable to both the customer and the manufacturer that the degradation of performance appear to the end user as being smoothly applied across all elements of a program, not appearing as though one element performs at a high speed and another unit at a degraded, compensating, low speed.
5) The degradation of a processor should allow for achievement of a wide range of degradation without changes in the basic procedure or complex measurements to achieve the selected level of degradation.
6) The time required to sample an interval of time in a processor performing an emulation does not in itself take zero time, so this is a subtle factor in both choosing and implementing the procedure for degradation.

Embodiments of the present invention address and resolve these considerations.

OBJECTS OF THE INVENTION

It is therefore a broad object of this invention to provide an improved computer processor derating procedure.

It is another object of this invention to provide such a procedure which is highly accurate in establishing a processor's submodel performance.

It is yet another object of this invention to provide such a procedure that is relatively simple and which itself constitutes a negligible load on system performance.

In another aspect, it is an object of this invention to provide such a procedure that, in various embodiments, can effectively accommodate and properly derate gating or "wait-type" instructions and also instructions which access the real time clock ("RTC-access-type" instructions).

SUMMARY OF THE INVENTION

Briefly, these and other objects of the invention are achieved by: sampling a real-time counter/clock (RTC) to obtain an initial time value $T1$; resetting an Icnt Counter; incrementing the Icnt Counter to reflect the processing of each instruction; comparing the count in the Icnt Counter to a predetermined count IcntMax and if the count in the Icnt Counter is at least IcntMax, then sampling the RTC to obtain a second time $T2$. $T1$ is then subtracted from $T2$ to obtain a time difference $DT$ which is multiplied by $((1-1/DF)-1)$ to obtain a Degradation Delay DD period, $DF$ being a degradation factor which is a constant having a value that is the ratio of the desired submodel performance with respect to full performance. The Degradation Delay is instituted by sampling the RTC from time to time to obtain a test third time $T3$. When test $T3$ minus $T2$ exceeds or equals $DD$, then $T1$ is set to the current value for $T3$, and the procedure is repeated for a next group of instructions.

Further accuracy can be achieved by remembering the difference between the quantity $T3$ minus $T2$, and $DD$ which is saved as DDExtra. DDExtra is the amount of time larger than $DD$ that has been delayed during a given pass through the process, and for further precision may be used during the next group of instructions to reduce the delay time; that is, the applied delay for this next group is $DD$ minus DDExtra from the previous group of instructions.

It is noted that the incrementing of the Icnt Counter and the comparison against the number IcntMax is a mechanism intended to trigger the periodic reading of the RTC. The reading of the RTC in most processors takes time which would significantly slow the processing, or the emulation if it was done during the processing of every instruction, which would be unacceptable with respect to overall performance. The incrementing of the Icnt Counter is intended to be a function of trivial performance impact, and this is all that happens in the normal case. When Icnt reaches IcntMax, then the time for the reading of RTC is reached, but since this determination is only made occasionally, it constitutes low overhead with greatly reduced impact on performance (IcntMax is large, for example 100 to 10000, or more).

It is further noted that the method described above of using an Icnt Counter and comparison of Icnt to IcntMax is for exemplary purposes only, and any mechanism which causes or allows only substantially periodic sampling of the RTC could be used.

In the repertoire of instructions for many processing units, there are instructions which allow delay, or which themselves read or use the RTC in some way. Precise degradation of performance for submodel offerings may optionally, for further accuracy, be achieved by considering and treating "wait-type" and/or "RTC-access-type" instructions specially.

"Wait" instructions tell the processor to stop and simply wait for something to do such as wait for an input/output operation to complete. This internal (to the instruction) waiting is completed when some external event, such as an interrupt, occurs or when some specified amount of delay is achieved. For "wait-type" instructions, best precision of delay is achieved if the internal wait loop is not entered until the Degradation Delay procedure as described above is immediately processed, just as though IcntMax had been reached. If the external event occurs, the internal wait loop is exited, and the Degradation Delay is truncated.

A second refinement particularly applicable to an emulated or firmware controlled processor is that when the processor desires to read any RTC ("RTC-access-type" instruction) for other purposes than degradation, then the Degradation Delay procedure is applied before the RTC to which the processor is referring is sampled so that processing of two back-to-back "read RTC" instructions will not be completed in an unnaturally small amount of time; "unnatural" in this context meaning as though the instructions were running in a full performance version of the processor emulation.

DESCRIPTION OF THE DRAWING

The subject matter of the invention is particularly pointed out and distinctly claimed in the concluding portion of the specification. The invention, however, both as to organization and method of operation, may best be understood by reference to the following description taken in conjunction with the subjoined claims and the accompanying drawing of which:

DESCRIPTION OF THE PREFERRED EMBODIMENT(S)

In the discussion below of the embodiments of the invention, the following definitions are used:

"DF" is a Delay Factor which defines the fraction of full performance that should be applied to obtain the desired submodel performance. For example, a value for DF of 0.75 would indicate that a processor is intended to perform at 75% of the processor's full performance capability.

"DD" is a Degradation Delay, that is, an amount of time to be delayed during a pass through the procedure as determined by equations described below.

"DT is the number of units of time since the Degradation Delay (DD) was last applied.

"IcntMax" is a selectable constant which is approximates the number of instructions processed between invocations of the performance degradation procedure. The value of Icnt-Max can be suitably set for any given processor with consideration that the larger the value of IcntMax that is used, the less frequent the overhead incurred by the sampling of RTC, but making it too large results in the code appearing to run in fast bursts followed by long delays which may be undersirable. IcntMax should be a large enough number so that the degradation procedure introduces a very low overhead in the processing of each instruction. An exemplary value for IcntMax in the range of 100–10000 (or even more) might be chosen. An IcntMax value of 100 would mean that reading the RTC would happen every 100 instructions which might be too often. The value of 10000 might be approaching too infrequent because 10,000 instructions allows quite a bit of processing to be done. A suitable setting of IcntMax can be determined by experiments on a given machine and under a given workload.

"DDExtra" is a calculated period correction factor employed in one embodiment of the invention to improve the accuracy of the process.

Figure 1:
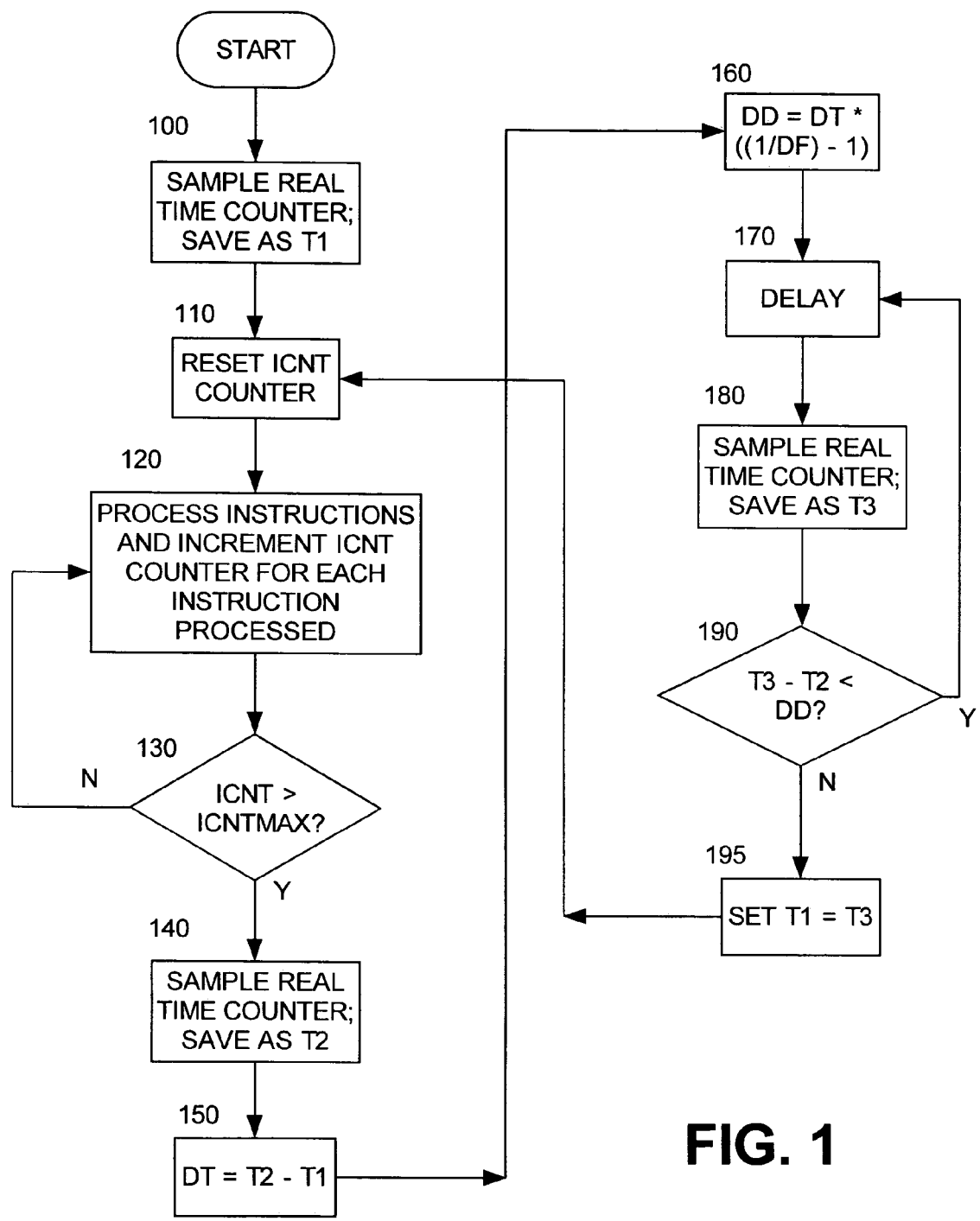
FIG. 1 is a process flowchart illustrating a basic implementation of the invention.

Referring now to FIG. 1, a flow chart is shown which describes a basic embodiment of the invention which can be used with both real and emulated processors.

At step 100, a real-time counter/real-time clock (the processor's RTC or another RTC maintained for the purpose) is sampled to obtain an initial T1 time, and at step 110, an Icnt Counter is reset. The Icnt Counter is a special purpose counter (typically implemented in software) which tracks the number of instructions processed during each pass through the algorithm shown in FIG. 1.

During steps 120 and 130, as each instruction is executed by the subject processor, the Icnt Counter is incremented, and its current count may be compared to IcntMax. When the current count reaches or exceeds IcntMax, step 130, then the delay aspect of the process will be entered such that the processor will "hold" for a suitable period. (It may be noted that step 130 need not necessarily be performed for each incrementation of the Icnt Counter. Step 130 can be performed "occasionally" such as every few milliseconds in order to avoid spending too much time on this step. Thus, the count in the Icnt Counter might exceed IcntMax by few counts when the decision is made at step 130 to enter the delay portion of the process by diverting process flow to step 140.)

At step 140, the RTC is sampled to obtain a value T2. Then, at step 150, DT is determined by solving the equation:

$$DT = T2 - T1$$

and, at step 160, the Degradation Delay is found by solving the equation:

$$DD = DT * ((1/DF) - 1).$$

Then, step 170 is entered to institute the Degradation Delay which is carried out by looping through steps 180 and 190 and back to step 170 for the DD period. Thus, at step 180, the RTC is sampled to determine the current T3. For each pass in this local loop, a decision is made at step 190 as to whether T3−T2<DD; if so, the Degradation Delay is not complete, and process flow returns to step 170. However, when T3 reaches a value at which T3−T2<DD is no longer true, then the Degradation Delay has completed this pass through the process. Thus, T1 is set to T3, step 195, and process flow returns to step 110 to start the processing of the next group of instructions. As noted above with respect to Icnt, step 190 need not necessarily be performed for each incrementation of T3. Steps 180 and 190 can be performed "occasionally" such as every few milliseconds in order to avoid spending too much time on these steps. Thus, T3 minus T2 might exceed DD by some amount when the decision is made at step 190 that the Degradation Delay is complete.

Figure 2:
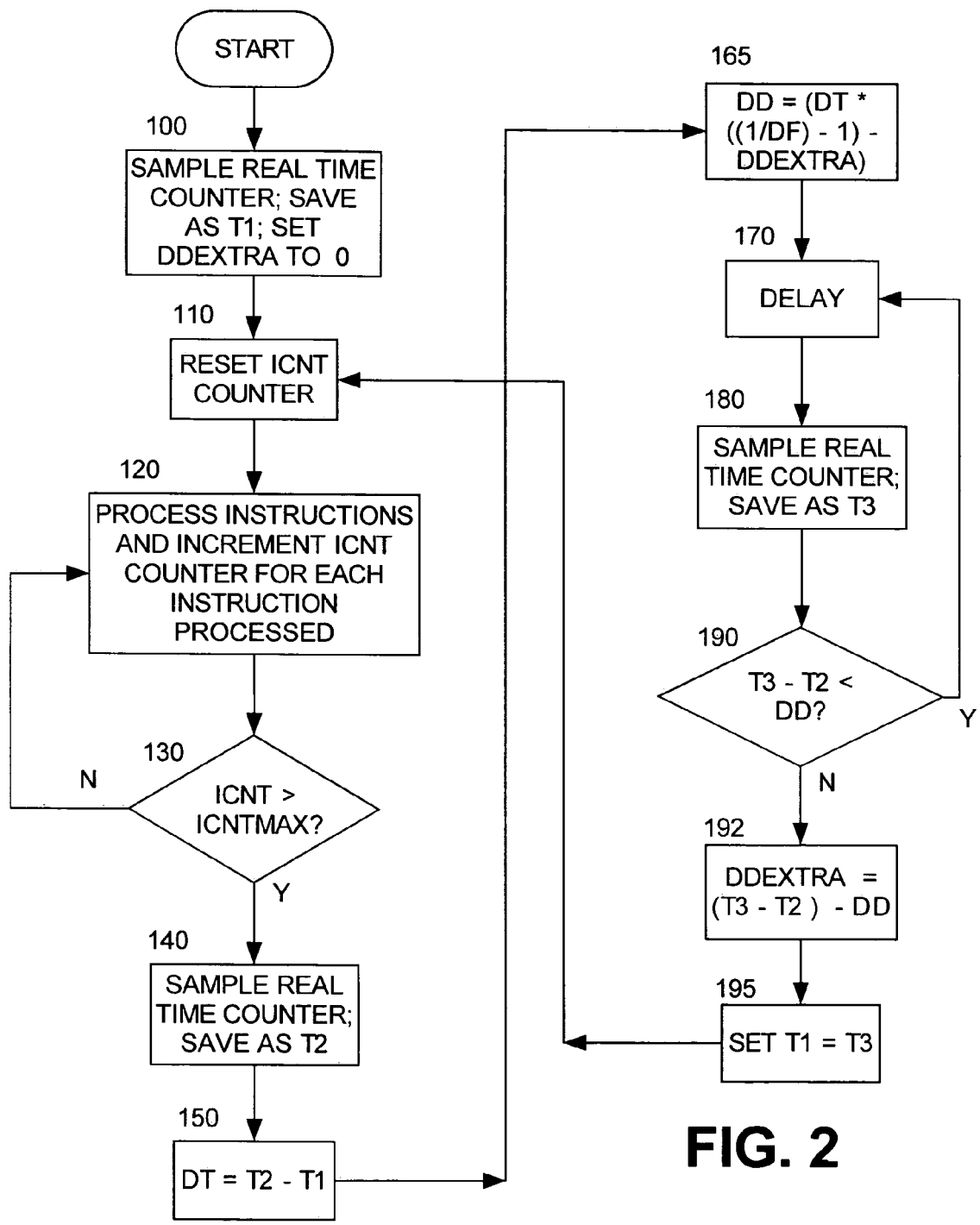
FIG. 2 is a process flowchart as in FIG. 1 but in which an enhancement in the algorithm is shown for better precision of degradation.

Referring now to FIG. 2, if the RTC is not sampled continuously at step 190, then the precision of the process can be improved by taking into account a value, DDExtra, which is the "extra" time spent in the current delay and subtracting this "extra" time from the next delay period. Thus, this correction factor is applied in a reiterative manner.

DDExtra is determined at step 192, which is interposed between steps 190 and 195, by calculating the period (T3−T2)−DD. Step 165 has been substituted for step 160 of FIG. 1 such that, for the next set of instructions, the new DD is calculated as (DT*((1/DF)−1)−DDExtra.

A refinement of the procedure takes into account the occurrence of instructions which are basically processor "wait-type"; i.e., instructions which direct the processor to stop and simply wait for something to do. An example is an instruction which is commonly used to invoke a wait for an input/output operation to complete and is awaiting an interrupt signal to that effect. This embodiment of the invention is shown in FIG. 3.

Figure 3:
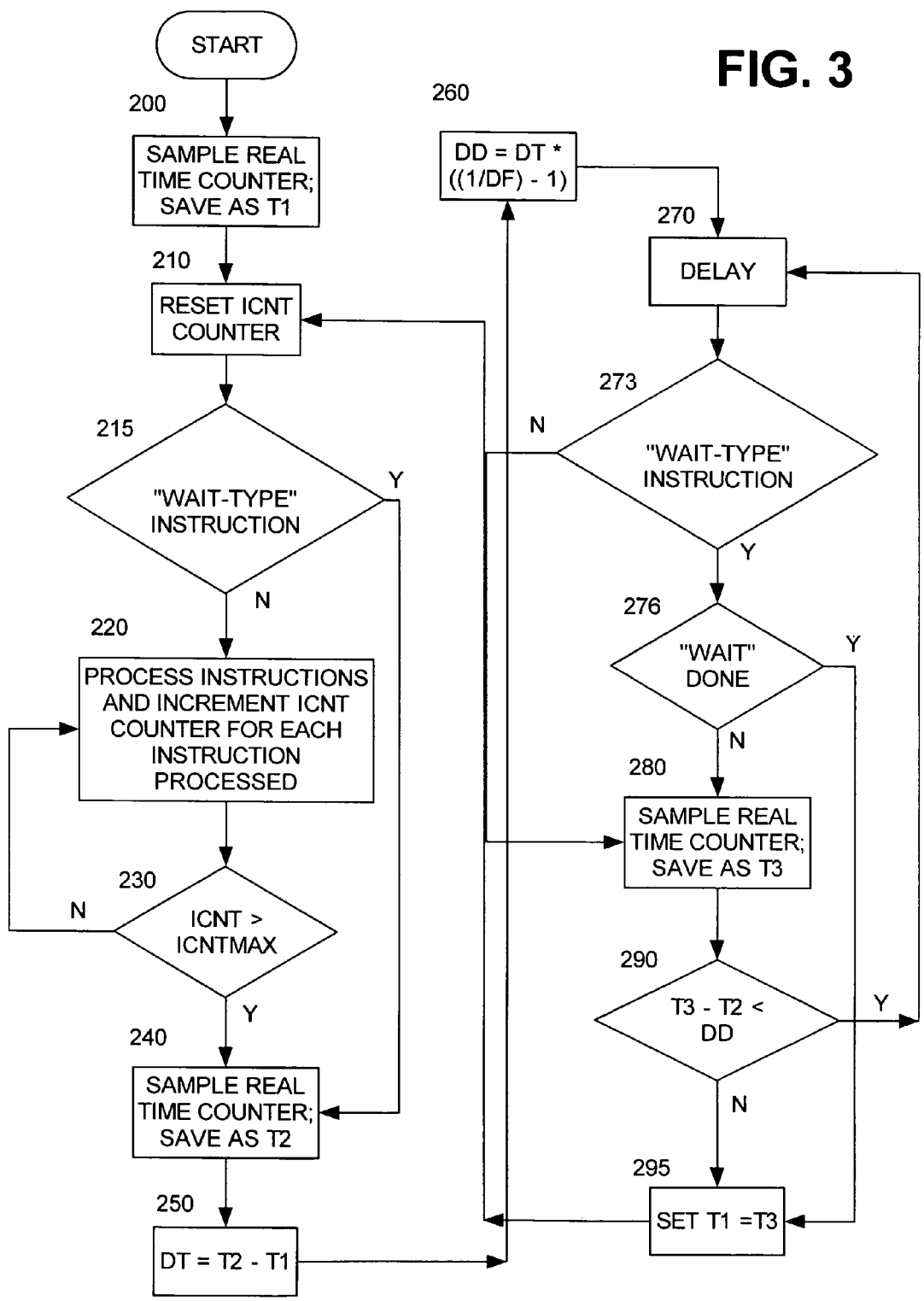
FIG. 3 is another process flowchart illustrating an implementation of the invention in which certain "wait-type" instructions are treated specially.

Thus, referring to FIG. 3, at step 200, a RTC is sampled to obtain an initial T1 time, and at step 210, an Icnt Counter is reset.

A test is made at step 215 to determine if each next instruction to execute is a "wait-type". If not, process flow goes to step 220.

During steps 220 and 230, each instruction (except for a "wait-type' instruction) is executed by the subject processor, the Icnt Counter is incremented and its current count may be compared to IcntMax. If the current count has reached or exceeded IcntMax, step 230, then the delay aspect of the process is entered by going to step 240. (As previously mentioned with respect to step 130 of FIG. 1, steps 225 and 230 can be performed "occasionally".)

However, if during step 215, it is determined that the next instruction is a "wait-type", then the process immediately enters the delay aspect of the process by going to step 240.

At step 240, the RTC is sampled to obtain a value T2. Then, at step 250, DT is determined by solving the equation:

$$DT=T2-T1$$

and, at step 260, the Degradation Delay is found by solving the equation:

DD=DT*((1/DF)−1) (or alternatively, as discussed in conjunction with FIG. 2 above, DD=(DT*((1/DF)−1)−DDExtra).

Then, step 270 is entered to institute the Degradation Delay. If the instruction is not a "wait-type", this operation is performed by looping through steps 273 (instruction is not a "wait-type"), 280 and 290 and back to step 270 for the DD period. At step 280, the RTC is sampled to determine the current T3. For each pass in this local loop, a decision is made at step 290 as to whether T3−T2<DD; if so, the Degradation Delay is not complete, and process flow returns to step 270. However, when T3 reaches a value at which T3−T2<DD is no longer true, then the Degradation Delay has completed for this pass through the process. T1 is set to T3, or a value which includes T3 as a factor, step 295, as previously described; and process flow returns to step 210 to restart the processing of instructions. (As noted above with respect to Icnt, step 290 need not necessarily be performed for each incrementation of T3. Steps 230 and 240 can be performed "occasionally" such as every few milliseconds in order to avoid spending too much time on these steps. Thus, the count in the T3 might exceed T2 by few counts when the decision is made at step 290 that the Degradation Delay is complete.)

However, if it is found at step 273 that the instruction is a "wait-type", then step 276 is entered to determine if the instruction's internal "wait" has completed. (For example, an interrupt signal would provide such information to indicate the end of a input/output operation wait.) If the instruction's internal "wait" is not done, then the process loops through steps 280 and 290 and back to step 270 as described above.

When it is determined at step 276 that the instruction's internal "wait" has completed, then process flow is directed to step 295 to develop a new T1 using T3 as a factor and then back to step 210 as previously described.

If DDExtra is taken into account as previously discussed, a step corresponding to step 192 of FIG. 2 can be inserted intermediate steps 290 and 295.

A second refinement particularly applicable to an emulated processor is that when the emulated processor itself desires to read any RTC, the delay procedure must be applied by the emulator before the RTC to which the processor is referring is sampled so that emulation of two back-to-back "read RTC" instructions will not be completed in an unnaturally small amount of time; "unnatural" in this context meaning as though the instructions were running in a full performance version of the processor emulation. This embodiment of the invention is shown in FIG. 4.

Figure 4:
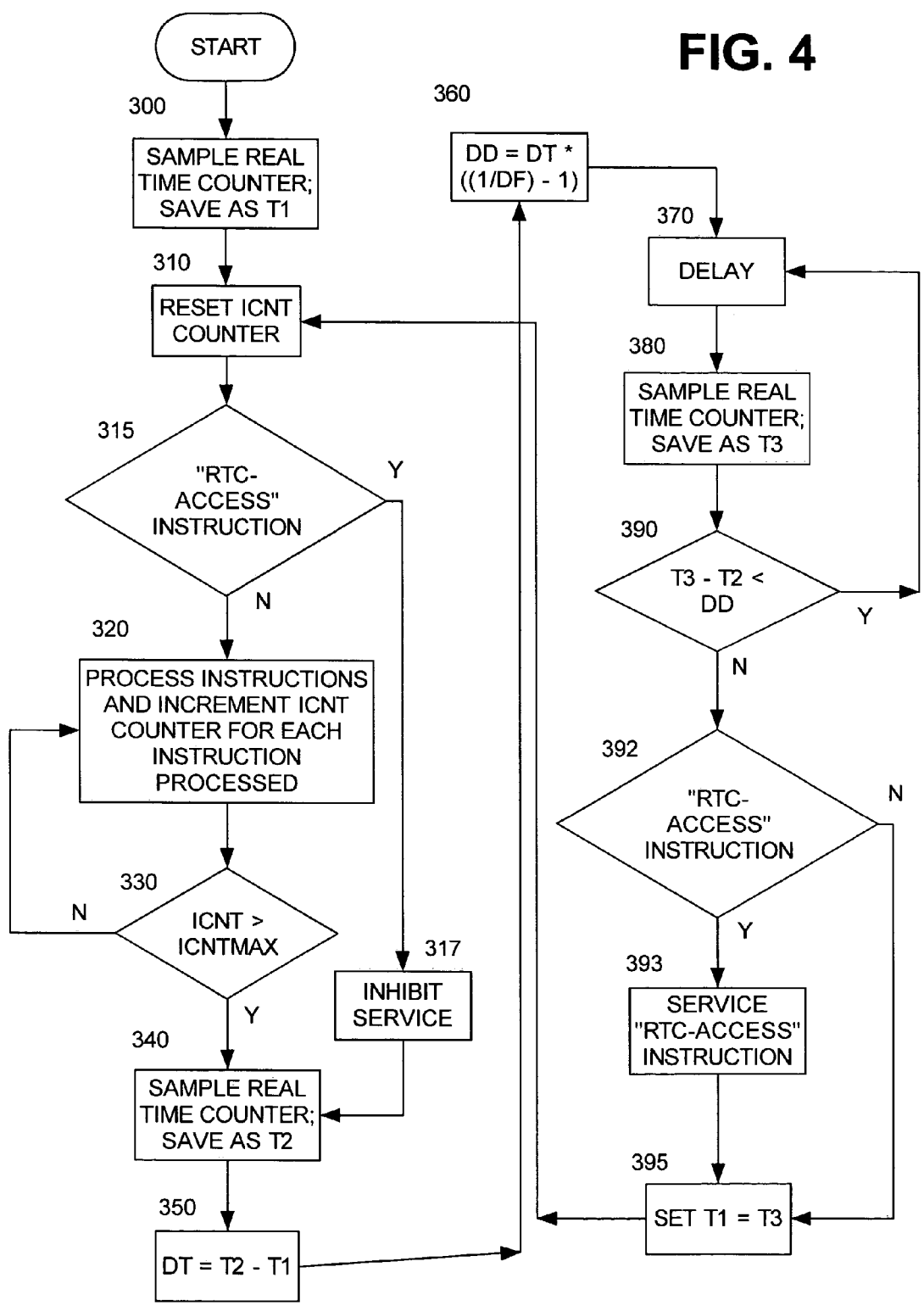
FIG. 4 is a process flowchart illustrating an implementation of the invention which prevents "unnaturally-short" flow through the process under certain conditions when the subject processor is emulated by another processor or by microprogram control.

Thus, referring to FIG. 4, at step 300, a RTC sampled to obtain an initial T1 time, and at step 310, an Icnt Counter is reset.

A test is made at step 315 to determine if each next instruction to execute is a "RTC-access-type"; i.e., the processor itself wishes to sample any RTC which could include the RTC from which T1, T2 and T3 are found. If not, process flow goes to step 320.

During steps 320 and 330, each instruction (except for a "wait-type' instruction) is executed by the subject processor, the Icnt Counter is incremented and its current count may be compared to IcntMax. If the current count has reached or exceeded IcntMax, step 330, then the delay aspect of the process is entered by going to step 340. As previously mentioned with respect to step 130 of FIG. 1, steps 325 and 330 can be performed "occasionally".

However, if during step 315, it is determined that the next instruction is a "wait-type", then the process immediately enters the delay aspect of the process by going to step 340.

At step 340, the RTC is sampled and a value T2 stored. Then, at step 350, DT is determined by solving by the equation:

$$DT=T2-T1$$

and, at step 360, the Degradation Delay is found by solving the equation:

DD=DT*((1/DF)−1) (or the alternative equation already discussed with respect to FIG. 2).

Then, step 370 is entered to institute the Degradation Delay which is carried out by looping through steps 380 and 390 and back to step 370 for the DD period. Thus, at step 380, the RTC is sampled to determine the current T3. For each pass in this local loop, a decision is made at step 390 as to whether T3−T2<DD; if so, the Degradation Delay is not complete, and process flow returns to step 370. However, when T3 reaches a value at which T3−T2<DD is no longer true, then the Degradation Delay has completed for this pass through the delay process.

At step 392, it is determined whether the current instruction is a "RTC-access-type"; if not, T1 is set to T3, step 395, and process flow returns to step 110 to restart the processing of instructions. As noted above with respect to Icnt, step 390 need not necessarily be performed for each incrementation of T3. (Steps 380 and 390 can be performed "occasionally". Thus, the count in the T3 might exceed T2 by few counts when the decision is made at step 390 that the Degradation Delay is complete.)

However, if it is found at step 392 that the instruction is a "RCT-access-type", then step 393 is entered to service the instructions own request for access to an RTC, and process flow is directed to step 395 and then back to step 310 as previously described.

Those skilled in the art will readily understand that the four embodiments of the invention can be combined in any suitable fashion for operation in a given computer system.

While the principles of the invention have now been made clear in an illustrative embodiment, there will be immediately obvious to those skilled in the art many modifications of structure, arrangements, proportions, the elements, materials, and components, used in the practice of the invention which are particularly adapted for specific environments and operating requirements without departing from those principles.

What is claimed is:

1. A process for limiting a performance of a processor to a selected submodel capability comprising the steps of:
   A) sample a Real Time Clock (RTC) to obtain a first time value T1;
   B) reset an Instruction Count (Icnt) Counter;
   C) determine if a current instruction is a "RTC-access-type";
      1) if the current instruction is not a "RTC-access-type", proceed to step D); and
      2) if the current instruction is a "RTC-access-type":
         a) inhibit service of the current instruction; and
         b) go to step F)
   D) process instructions while incrementing the Icnt Counter to reflect the processing of each instruction;
   E) compare the count in the Icnt Counter to a predetermined count Instruction Count Maximum (IcntMax); and
      1) if the count in said Icnt Counter is less than IcntMax, then return to step C); and
      2) if the count in said Icnt Counter is at least IcntMax, then proceed to step F);
   F) sample the RTC to obtain a second time T2;
   G) subtract T1 from T2 to obtain a time difference DT;
   H) multiply DT by $((1-1/DF)-1)$ to obtain a Degradation Delay DD period, DF being a constant having a value which is a desired submodel performance with respect to full performance;
   I) delay;
   J) during step I):
      1) sample the RTC to obtain a test third time T3;
      2) it test third time T3 minus T2 is less than DD, then continue step I); and
   K) determine if the current instruction is a "RTC-access-type";
   L) if the current instruction is not a "RTC-access-type", go to step N);
   M) service the "RTC-access-type" instruction;
   N) set T1 equal to T3 as used in step I) 2); and
   O) go to step B).

2. The process of claim 1 in which the value of IcntMax is at least 100.

* * * * *